United States Patent [19]

Kanner et al.

[11] 4,384,131
[45] May 17, 1983

[54] PROCESS FOR THE PREPARATION OF OXIMATOHYDRIDOSILANES AND AMINOXYHYDRIDOSILANES

[75] Inventors: Bernard Kanner, West Nyack; Steven P. Hopper, Mahopac, both of N.Y.

[73] Assignee: Union Carbide Corporation, Danbury, Conn.

[21] Appl. No.: 397,814

[22] Filed: Jul. 13, 1982

[51] Int. Cl.³ .................. C07F 7/10; C07F 7/18
[52] U.S. Cl. ................................................ 556/422
[58] Field of Search ........................................ 556/422

[56] References Cited

U.S. PATENT DOCUMENTS 3,448,136  6/1969  Pande et al. ............... 556/422 X
4,126,630  11/1978  Müller et al. .............. 556/422 X

FOREIGN PATENT DOCUMENTS 239144  3/1969  U.S.S.R. ....................... 556/422
494384  8/1976  U.S.S.R. ....................... 556/422

Primary Examiner—Paul F. Shaver
Attorney, Agent, or Firm—Paul W. Leuzzi

[57] ABSTRACT

A process whereby silanes of the general formula $$HSi(NRR^I)_x(R^{II})_{3-x}$$

are reacted in the presence of a catalyst with oximes or hydroxylamines in the stoichiometry of approximately one equivalent of oxime or hydroxylamine per mole of silicon-nitrogen linkage to give unexpectedly high yields of substituted silanes.

13 Claims, No Drawings

PROCESS FOR THE PREPARATION OF OXIMATOHYDRIDOSILANES AND AMINOXYHYDRIDOSILANES

CROSS-REFERENCE TO RELATED APPLICATION

The subject matter of this application is related to that of U.S. patent application Ser. No. 397,815, to Kanner et al. and filed on even date herewith, entitled: IMPROVED PROCESS FOR THE PREPARATION OF ALKOXYHDRIDOSILANES.

BACKGROUND OF THE INVENTION

The preferential displacement of silicon-nitrogen bonds in a compound that additionally contains silicon-hydrogen bonds is unknown in the art. What is well known is the preferential displacement of silicon-chlorine bonds in a compound containing silicon-hydrogen bonds. This latter reaction is characterized by side reactions and massive amounts of hydrochloric acid by product. To overcome these problems a new process is needed.

The insertion of carbon dioxide into the silicon nitrogen bond to give silyl carbamates was initially studied in the early sixties. Originally it was proposed that the insertion was effected by the displacement of the amine by a carbamic acid derivative rather than a direct two atom insertion. However, it has been noted that trisilylamine and methyldisilylamine do not appear to react with carbon dioxide. Surprisingly, the present process differs from the large body of published work in that one to three amino groups may be displaced from silicon and the displacement occurs from a silane bearing a silicon hydrogen bond and that the silicon hydrogen bond is not attacked. Thus in this catalyzed process, the initial formation of a silylcarbamate linkage seems most reasonable. The silyl carbamate may be formed either by a direct two atom insertion by carbon dioxide or by the interaction of the silyl amine with a carbamate derivative. The greater reactivity of the silyl carbamate linkage versus a silyl amine linkage toward nucleophilic displacement by an alcohol leading to the formation of alkoxysilanes was noted in U.S. Pat. No. 3,792,073; U.S. Pat. No. 3,816,359; and U.S. Pat. No. 3,906,018.

In 1975 the reaction of N,O-bis-(trimethylsilyl)carbamate with alcohols, phenols and carboxylic acids was reported to lead to the formation of trimethylalkoxy (and acetoxy) silanes, carbon dioxide and ammonia. (L. Berkofer and P. Sommer, J. Organometal Chem., 99 (1975) Cl.). While the literature thus far cited is related to the process of this invention, the use of reactions of silyl carbamate linkages to carry out nucleophilic substitution reactions with alcohols with the retention of the labile silicon hydrogen linkage went unrecognized. In addition the catalyzed reactions described herein have a significant advantage over the currently taught and practiced art. For example, the commonly used method for the preparation of trialkoxysilane suffers from several disadvantages that can be circumvented by this invention. The current art is characterized by the following: (a) solvent is sometimes employed, (b) the reaction time is relatively long in order to minimize formation of tetra-alkoxysilanes and (c) hydrochloric acid is produced.

As the process is currently understood it appears to offer a new, convenient and high yield synthesis of alkoxysilanes and trialkoxysilanes in particular. It seems most likely that the process involves intermediate silyl carbamate linkages which appear to be enormously reactive toward displacement by alcohols when compared to silyl amine linkages or the silicon hydrogen bond.

The catalyzed process described here is clearly superior for the preparation of trialkoxysilanes in that it does not require solvent, it involves short reaction times and moderate temperatures, the displaced amine is much less corrosive than hydrogen chloride, and proceeds with remarkable and unexpected selectivity for the formation of trialkoxysilanes.

SUMMARY OF THE INVENTION

The instant invention provides a process for reacting silanes of the general formula:

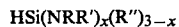
$$HSi(NRR')_x(R'')_{3-x} \qquad I$$

wherein R, R' and R'' may be aliphatic or aromatic, saturated or unsaturated, hydrocarbon radicals, substituted hydrocarbon radicals having from one to eight carbon atoms, inclusive, and R, R' only may also be hydrogen and R'' may also be alkoxy and x ranges from one to three, with oximes or hydroxylamines in the stoichiometry of approximately one equivalent of oxime or hydroxylamine per mole of silicon nitrogen linkage in the presence of a catalyst. The reaction results in unexpectedly high yields of substituted silanes of the general formula I where the silyl amine groups have been replaced by alkoxide groups without significant loss of the silicon-hydrogen. Similar reactions in the absence of a catalyst result in undesirably low yields of the corresponding alkoxy silanes and, in most cases, very substantial loss of the silyl hydrogen. The critical aspect of the catalytic process is the virtually complete retention of the silicon hydrogen linkage in the product(s).

DETAILED DESCRIPTION OF THE INVENTION

In accordance with the present invention there is provided a novel reaction between the silanes of formula I and oximes or hydroxylamines to provide oximatohydridosilanes or aminohydridosilanes in high yield.

The silanes generally believed to be useful in the process of the present invention are represented by the general formula:

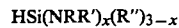
$$HSi(NRR')_x(R'')_{3-x} \qquad (I)$$

wherein R, R' and R'' are independently an aliphatic or aromatic, substituted or unsubstituted, saturated or unsaturated hydrocarbon radicals having from one to eight carbon atoms inclusive and where R and R' may also be hydrogen and R'' may also be alkoxy and where x has a value of from one to three. Preferably, R, R' and R'' are independently an aliphatic, unsubstituted, saturated or unsaturated hydrocarbon radical having one to six carbon atoms, inclusive and x is two or three. Most preferably, the R and R' are each a methyl group and x is three.

Suitable silanes of formula I which may be employed in the invention process include, but are not limited to, dimethylaminomethylethylsilane, diethylamino-methylpropylsilane, methylaminomethylethylsilane, ethylaminomethylethylsilane, phenylaminomethylethylsilane, benzylaminomethylphenylsilane, diphenylaminomethylphenylsilane, dibenzylaminomethyl-phenylsilane, dimethylaminodimethylsilane, diethylaminodimethylsilane, methylaminodimethyl-silane, ethylaminodimethylsilane, diphenylaminodi-methylsilane, dibenzylaminodimethylsilane, phenylaminodimethylsilane, benzylaminodimethylsilane, bis-dimethylaminomethylsilane, bis-diethylaminomethylsilane, bis-methylaminoethylsilane, bis-ethylaminoethylsilane, bis-diphenylaminomethylsilane, bis-benzylaminomethylsilane, bis-phenylaminomethylsilane, bis-benzylaminomethylsilane, bis-dimethylaminophenylsilane,- bis-diethylaminophenylsilane, bis-ethylaminophenylsilane, bis-ethylaminopropylsilane, bis-diphenylaminopropylsilane, bis-dibenzylaminopropylsilane, tris-dimethylaminosilane, tris-diethylaminosilane, tris-methylaminosilane, tris-ethylaminosilane, tris-diphenylaminosilane, tris-dibenzylaminosilane, tris-phenylaminosilane, tris-benzylaminosilane, dicyclopentylaminomethylethylsilane, cyclopentylaminodimethylsilane, dicyclohexylaminodimethylsilane, cyclohexylaminodimethylsilane, bis-dicyclopentylaminomethylsilane, bis-cyclopentylaminomethylsilane, dicyclopentylaminodiphenylsilane, bis-dicyclopentylaminophenylsilane, tris-dicyclopentylaminosilane, cyclohexylaminodiphenylsilane, bis-cyclohexylaminomethylsilane, tris-cyclohexylaminosilane, tris(piperidino)silane and the like. Preferably the silane is tris(dimethylamino)silane.

The oximes generally believed to be useful in the process of the present invention are represented by the general formula:

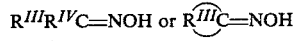  (II)

wherein $R^{III}$ and $R^{IV}$ are independently an aliphatic or aromatic, substituted or unsubstituted, saturated or unsaturated hydrocarbon radical having from one to twelve carbon atoms, inclusive and $R^{III}$ and $R^{IV}$ can be hydrogen but not both. Preferably, $R^{III}$ and $R^{IV}$ are independently an aliphatic, unsubstituted, saturated or unsaturated hydrocarbon radical having one to six carbon atoms, inclusive.

Suitable oximes which may be employed in the instant process include, but are not limited to, $CH_3CH=NOH$, $(CH_3)_2C=NOH$, $(C_2H_5)_2C=NOH$, $(CH_3)(C_2H_5)C=NOH$, $(n-C_3H_7)CH=NOH$, $(i-C_3H_7)_2C=NOH$, $(n-C_4H_9)_2C=NOH$, $(t-C_4H_9)CH=NOH$, $(t-C_4H_9)(CH_3)C=NOH$, $(C_6H_5)CH=NOH$, $(C_6H_5)_2C=NOH$, $(C_6H_5)(CH_3)C=NOH$, $(CH_3C_6H_4)_2C=NOH$, $(cyclo-C_6H_{11})CH=NOH$, $(cyclo-C_5H_9)_2C=NOH$, and the like.

The hydroxylamines generally believed to be useful in the process of the present invention are represented by the general formula:

  (III)

wherein $R^{III}$ and $R^{IV}$ are independently of the same significance as set forth above. Suitable hydroxylamines which may be employed in the instant process include, but are not limited to, $CH_3NHOH$, $(CH_3)_2NOH$, $(C_2H_5)NHOH$, $(CH_3)(C_2H_5)NOH$, $(n-C_3H_7)NHOH$, $(i-C_3H_7)_2NOH$, $(n-C_4H_9)_2NOH$, $(t-C_4H_9)NHOH$, $(t-C_4H_9)(CH_3)NOH$, $(C_6H_5)NHOH$ $(C_6H_5)_2NOH$, $(C_6H_5)(CH_3)NOH$, $(CH_3C_6H_4)NOH$, $(Cyclo-C_6H_{11})NHOH$, $(Cyclo-C_5H_9)NOH$, and the like.

The process is a catalyzed one and the catalyst may be carbon dioxide, carbonoxy sulfide, carbon disulfide or amine complexes thereof. Some examples of amine complexes which are effective in the above process include, but are not limited to, dimethylammonium dimethylcarbamate, diethylammonium, diethylcarbamate, dipropylammonium dipropylcarbamate, dibutylammonium dibutylcarbamate, ammonium carbamate, methylammonium methylcarbamate, diphenylammonium diphenylcarbamate, phenylammonium phenylcarbamate, benzylammonium benzylcarbamate, dibenzylammonium dibenzylcarbamate, dimethylammonium diethylcarbamate, diethylammonium dimethylcarbamate, methylammonium ethylcarbamate, diphenylammonium dimethylcarbamate, dimethylammonium diphenylcarbamate, diethylammonium dibenzylcarbamate, dibenzylammonium diethylcarbamate, phenylammonium dimethylcarbamate, methylammonium diphenylcarbamate and the like.

In addition the following classes of catalysts may be employed to an equal or lesser advantage. Strong protic acids such as hydrohalic acids, for example hydrochloric acid, hydrobromic acid and hydroiodic acid; sulfuric acids, for example sulfuric acid and para-toluene-sulfonic acid; and others such as haloacetic acids for example trifluoroacetic acid. Lewis acids such as aluminum trichloride and ferric chloride may be used as a catalyst for the process to a lesser advantage than the catalysts listed above. In addition, certain carboxylic acids, such as acetic acid and its substituted derivatives, and salts derived therefrom, such as ammonium acetate, may be used as catalysts for the process.

The catalyst concentration employed in the instant process should be between about 0.01 to 10 mole percent of the silicon-nitrogen bonds sought to be esterified. It is preferred for the purpose of this invention to maintain the catalyst concentration between about 0.1 and 3 mole percent. Although higher and lower limits are possible no particular advantages are seen from higher, and thus costlier, concentrations and the lower concentrations may lead to some loss of the silicon-hydrogen linkage sought to be preserved.

The reaction conditions are such that the catalyzed reaction may be carried out with or without solvent. In most cases there is no particular advantage to utilizing a solvent. However, in cases where a solvent is desirable for some reason, such as solubility or temperature control, a solvent may be used. If a solvent is used, it should not contain an active hydrogen such as are found in alcohols and amines. Suitable solvents are exemplified by hydrocarbons or ethers such as hexane, toluene, diethylether, tetrahydrofuran and the like.

Additionally, the temperature is normally kept between 0° C. and 60° C. but the process could be run anywhere from −50° C. up to 150° C. and under special circumstances, perhaps higher. Due to the ease of the process there is no special advantage in operating at higher conditions of temperature.

The stoichiometry of the alcohol to the silicon-nitrogen linkage generally should not substantially exceed one in order to avoid substantial loss of the silyl-hydrogen linkage. Slight excess over stoichiometry may be desirable to keep the level of unreacted silicon-nitrogen groups to a minimum. In cases where it is desirable to prepare and isolate mixed aminoalkoxysilanes the stoichiometry of alcohol to silyl-amine linkage is generally less than one.

The order of addition of the reagents is important to the process described above. The reagents should be mixed in such a way as to avoid an excess of oximes or hydroxylamines with respect to the silicon nitrogen linkage. It is therefore not advisable to add the aminosilane to the alcohol. Generally the catalyst is added to the silylamine or its solution prior to adding the alcohol but the catalyst may be present wholly or partially in the oxime or hydroxylamine or its solution.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

EXAMPLES

The following abbreviations are used in the examples which follow:
TRIS: tris(dimethylamino)silane
DI-CARB: dimethylammonium dimethylcarbamate

Example One

Preparation of Tris (diethylaminoxy) silane

A 50 ml, round bottomed, three necked flask equipped with a magnetic stirring unit, thermometer, constant pressure addition fullel and a reflux condenser topped with a nitrogen inlet tube was flushed with nitrogen. To the flask was then added 9.2 gm (57 mmole) of tris(dimethylamino)silane and 400 microliters of dimethylammonium dimethylcarbamate. Diethylhydroxylamine, 15.2 gm (171 mmole) was added dropwise with stirring under nitrogen over a period of twenty minutes. The mildly exothermic reaction raised the temperature of the reaction mixture from 23° to a maximum of 32° C. during the course of the addition. After cooling to room temperature, the reaction was examined by nmr. The crude material, 16.4 gm (98%) gave a nmr spectrum wholly in accord with the title silane. The crude product from a duplicate run was added to the material and the combined reaction mixtures were vacuum distilled. Of the 32.4 gm of combined materials 22.6 gm (68%) was collected with a bp of 97–98% /0.6 mm. Examination of the pot residue, 6.0 gm of viscous liquid and 3.4 gm of solid material, by glpc indicated the presence of an additional 1.2 gm of product. The product was identified by the following data:
b.p. 97–98°/0.6 mm
I.R. 2240 cm$^{-1}$, Si—H
Anal. Calcd. C, 49.11; H, 10.65 Found C, 49.47, H, 10.44

NMR (CCl$_4$ with internal standard HClC=CCl$_2$) δ4.57, s, 1.1H, Si—H, 2.84, q, 12.8H, —CH$_2$CH$_3$, J=8 Hz, and 1.07 ppm, t, 17.1 H, —CH$_3$, J=8 Hz.

Mass spectrum - m/e (% abundance, assignment) 205 (82.3 M+ $^{O-}$ONEt$_2$); 136 (100, C$_3$H$_{10}$NO$_3$Si), 134 (66, C$_3$H$_{10}$N$_2$O$_2$Si), 132 (66, C$_3$H$_{10}$O$_3$Si), 120 (32, C$_3$H$_{10}$NO$_2$Si)

Example Two

Preparation of Tris (dimethyloximato) silane

A 100 ml, round bottomed, three necked flask equipped with a magnetic stirring unit, constant pressure addition funnel, thermometer and a reflux condenser topped with a nitrogen inlet tube was flushed with nitrogen. The flask was then charged with 8.4 gm (2.1 mmole) of tris(dimethylamino) silane and 100 microliters of dimethylammonium dimethylcarbamate. An ether solution, 60 ml, of 11.4 gm (156.2 mmole) of acetone oxime was added dropwise with stirring over a period of 35 minutes. Six minutes after the addition was started the temperature had risen to 28° and remained at that temperature during the balance of the addition. The reaction mixture was analyzed by glpc shortly after the completion of the addition—little if any starting material remained. The ether was removed by rotary evaporation. The crude product of 12.7 gm (98%) was a gold viscous liquid that gave a single peak on glpc analysis. The nmr spectrum of the crude material was identical to that of the distilled material described below.

The crude product was vacuum distilled through a short path distillation column. The distillation was accompanied by some decomposition and was discontinued after the collection of 7.8 gm (62%) of glpc pure material identified as the title silane by the following data. The distillation pot contained 2.4 gm of undistilled material.
b.p. 101°–102°/0.25 mm
NMR δ4.87, s, 0.7H, SiH and 1.87 ppm, s 18.3H, Ch$_3$
I.R. 2220 cm$^{-1}$, SiH and 1640 cm$^{-1}$, —C=N—
Anal. Calcd. C, 44.06; H, 8.04. Found C, 43.88; H, 8.04

Mass Spectrum - m/e (% abundance, assignment) 245 (16, M+), 244 (100, M+ −1), 189 (33, M+—N=CMe$_2$), 134 (75,(HO)$_2$SiON=CMe$_2$+)

Examples Three Through Nine

Table One contains additional examples of the process being claimed. In addition Table One contains examples where the catalyst was omitted and unreacted tris(dimethylamino)silane was observed. This latter observation implies loss of the silicon hydrogen functionality. The reactions in examples three through nine were carried out in fashion quite similar to that described for examples One and Two.

TABLE ONE

REACTIONS OF TRIS(DIMETHYLAMINO) SILANE WITH THREE EQUIVALENTS OF HYDROXYLCONTAINING NUCLEOPHILE CATALYZED BY DIMETHYLAMMONIUM DIMETHYLCARBAMATE

| Example | Catalyst | Nucleophile | Unreacted Tris | Product | Crude Yield | Distilled Yield |
|---|---|---|---|---|---|---|
| 3 | No | acetone oxime | 19% | [(CH$_3$)$_2$C=N—O]$_3$SiH | — | — |
| 4 | Yes | 2-butanone oxime | — | (CH$_3$CH$_2$C(CH$_3$)=N—O—)$_3$SiH | 95% | 57% |
| 5 | No | 2-butanone oxime | 12% | (CH$_3$CH$_2$C(CH$_3$)=N—O—)$_3$SiH | — | — |
| 6 | Yes | 2-hexanone oxime | — | (CH$_3$CH$_2$CH$_2$CH$_2$C(CH$_3$)=N—O)$_3$SiH | 99% | 6% |
| 7 | No | 2-hexanone oxime | 19% | (CH$_3$CH$_2$CH$_2$CH$_2$C(CH$_3$)=N—O)$_3$SiH | — | — |

TABLE ONE-continued
REACTIONS OF TRIS(DIMETHYLAMINO) SILANE WITH THREE EQUIVALENTS OF HYDROXYLCONTAINING NUCLEOPHILE CATALYZED BY DIMETHYLAMMONIUM DIMETHYLCARBAMATE

| Example | Catalyst | Nucleophile | Unreacted Tris | Product | Crude Yield | Distilled Yield |
|---|---|---|---|---|---|---|
| 8 | Yes | Ethyl acetate oxime | — | $(CH_3CH_2O-\underset{\underset{CH_3}{\|}}{C}=N-O)_3SiH$ | 84% | — |
| 9 | No | Dimethylhydroxylamine | 70% | | — | — |

We claim:

1. A process for the preparation of oximatohydridosilanes and aminoxyhydridosilanes which comprises reacting a silane of the general formula $$HSi(NRR^1)_x(R^2)_{3-x}$$

wherein R, $R^1$ and $R^2$ are independently an aliphatic or aromatic, substituted or unsubstituted, saturated or unsaturated hydrocarbon radical having from one to eight carbon atoms inclusive and where R and $R^2$ may also be hydrogen and where $R^2$ may also be alkoxy where x has a value of from one to three with oximes or hydroxylamine of the general formula $R^3R^4C=NOH$ (1)

=NOH (2)

$R^3R^4NOH$ (3)

OH (4)

where $R^3$ and $R^4$ are independently an aliphatic or aromatic, saturated or unsaturated, substituted or unsubstituted hydrocarbon radical having from one to twelve carbon atoms inclusive in the presence of a catalyst at a temperature between −50° C. to 150° C. where approximately one equivalent of alcohol is present per mole of the silicon-nitrogen bond and where the catalyst concentration is equal to about 0.01 to 10 mole percent of the silicon-nitrogen bonds.

2. The process of claim 1 wherein R, $R^1$ and $R^2$ of the silane and $R^3$ and $R^4$ of the oxime or hydroxylamine are independently an aliphatic, unsubstituted, saturated or unsaturated hydrocarbon radical having one to six carbon atoms inclusive.

3. The process of claim 1 wherein x of the silane is three.

4. The process of claim 1 wherein the reaction temperature is between 0° C. and 60° C.

5. The process of claim 1 wherein the catalyst concentration is between 0.1 and 3 mole percent of the silicon-nitrogen bonds.

6. A process for the preparation of oximatohydridosilanes and aminoxyhydridosilanes which comprises reacting a silane of the general formula $$HSi(NRR^1)_x(R^2)_{3-x}$$

with an oxime or hydroxylamine of the general formula $R^3R^4C=NOH$ (1)

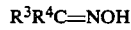=NOH (2)

$R^3R^4NOH$ (3)

OH (4)

wherein R, $R^1$, $R^2$, $R^3$ and $R^4$ are independently an aliphatic, unsaturated, unsubstituted, hydrocarbon radical having one to six carbon atoms inclusive and R and $R^1$ may also be hydrogen, x has a value of from one to three, in the presence of a catalyst at a temperature from −50° C. to 150° C. where the catalyst is present in an amount equal to from 0.01 to 10 mole percent of the silicon-nitrogen bond and there is approximately one equivalent of alcohol per mole of the silicon-nitrogen bonds.

7. The process of claim 6 wherein R, $R^1$ and $R^2$ of the silane are each methyl groups.

8. The process of claim 7 wherein x is equal to 3.

9. The process of claim 6 wherein the temperature is between about 0° and 60° C.

10. The process of claim 6 wherein the catalyst concentration is between about 0.1 and 3 moles percent.

11. The process of claim 6 wherein the silane is trisdimethylaminosilane, the temperature is between about 0° C. to 60° C., the catalyst is dimethylammonium dimethylcarbamate and at a catalyst concentration of about 0.1 to 3 mole percent.

12. The process of claims 1 or 6 wherein the catalyst is carbon dioxide.

13. The process of claims 1 or 6 wherein the catalyst is acetic acid.

* * * * *